United States Patent [19]

Lapidus et al.

[11] Patent Number: 5,185,084
[45] Date of Patent: Feb. 9, 1993

[54] METHOD AND APPARATUS FOR CONTROL OF FLOW THROUGH A FILTER CHAMBER BY MEASURED CHAMBER EQUILIBRATION PRESSURE

[75] Inventors: Stanley N. Lapidus; Dean Kamen; Richard R. Villeneuve, all of Bedford, N.H.; Lewis T. Polk, Jr., Bedford, Mass.

[73] Assignee: Cytyc Corporation, Marlborough, Mass.

[21] Appl. No.: 717,090

[22] Filed: Jun. 18, 1991

Related U.S. Application Data

[62] Division of Ser. No. 487,637, Mar. 2, 1990, abandoned.

[51] Int. Cl.⁵ .............................................. B01D 17/12
[52] U.S. Cl. ...................................... 210/741; 210/90; 210/97; 210/808; 422/81; 422/101; 73/61.47; 436/177
[58] Field of Search ............................ 604/65, 67, 406; 128/DIG. 12, DIG. 13; 210/90, 134, 808, 321.65, 741, 141, 143, 97; 422/81, 82, 101; 436/63, 177, 178; 137/14, 488; 73/61.47

[56] References Cited

U.S. PATENT DOCUMENTS

| | | | |
|---|---|---|---|
| 3,658,478 | 4/1972 | Spergel et al. | 422/81 |
| 3,900,290 | 8/1975 | Hornstra | 210/90 |
| 4,137,915 | 2/1979 | Kamen | 128/DIG. 13 |
| 4,303,533 | 12/1981 | Fremont | 210/791 |
| 4,335,206 | 6/1982 | Wilkins et al. | 435/34 |
| 4,395,493 | 7/1983 | Zahniser et al. | 435/289 |
| 4,410,164 | 10/1983 | Kamen | 251/9 |
| 4,411,649 | 10/1983 | Kamen | 128/DIG. 13 |
| 4,435,507 | 3/1984 | Steakvist | 436/177 |
| 4,449,976 | 5/1984 | Kamen | 137/192 |
| 4,583,396 | 4/1986 | Hunt et al. | 73/61.47 |
| 4,614,716 | 9/1986 | Rohrback | 435/291 |
| 4,634,426 | 1/1987 | Kamen | 604/65 |
| 4,695,382 | 9/1987 | Cronin | 604/406 |
| 4,740,200 | 4/1988 | Theeuwes | 604/406 |
| 4,778,450 | 10/1988 | Kamen | 604/65 |
| 4,778,451 | 10/1988 | Kamen | 604/67 |
| 4,808,161 | 2/1989 | Kamen | 604/67 |
| 4,816,019 | 3/1989 | Kamen | 604/65 |
| 4,826,482 | 5/1989 | Kamen | 128/DIG. 13 |

FOREIGN PATENT DOCUMENTS 2054200  2/1981  United Kingdom ....... 128/DIG. 13
87/05224  9/1987  World Int. Prop. O. .

OTHER PUBLICATIONS

Kroner et al., (1984), Analytica Chimica Acta 163: 3–15.
European Search Report corresponding to European Patent Application No. 90125586, Apr. 12, 1991.

Primary Examiner—Robert A. Dawson
Assistant Examiner—Joseph Drodge
Attorney, Agent, or Firm—Lahive & Cockfield

[57] ABSTRACT

A method and apparatus for the controlled instrumentation processing of cells and other paricles with a filter device measures a parameter of the flow through the filter device of a fluid carrying the particles. A measure of the change of fluid flow through the filter device yields desired information for quantizing the particles and for quantizing the obstruction of the filter device by the particles. The method and apparatus typically operate automatically.

7 Claims, 2 Drawing Sheets

METHOD AND APPARATUS FOR CONTROL OF FLOW THROUGH A FILTER CHAMBER BY MEASURED CHAMBER EQUILIBRATION PRESSURE

This is a division of application Ser. No. 487,637, filed Mar. 2, 1990 now abandoned.

BACKGROUND

This invention relates, in one instance, to measuring the quantity or concentration of cells in a biological sample. The invention is useful in anatomic pathology, which is a medical and laboratory specialty that makes diagnoses on findings in human tissues and cells.

More broadly, the invention provides a method and apparatus for the controlled instrumented processing of particles with a filter device. The filter device is of the screen type, e.g. a membrane filter, that blocks particles larger than a threshold size and passes smaller particles. The particles of interest are carried in a fluid, and a change in the flow of the liquid carrying the particles, due to blockage of the filter device by the particles, provides information of interest both regarding the blockage of the filter and regarding the particles.

The invention thus provides quantitative instrumentation information regarding particles, generally of unknown particles, by an indirect technique that measures a flow condition of a screen-type filter device in the flow path of a fluid that carries the particles.

One application of the invention is in the pathological test, termed a Pap smear test, that examines cells for the presence of cancer. An established procedure for this test transfers a measured quantity of cells from a biological sample to a microscope slide for examination. One prior procedure for obtaining the desired measured quantity of cells from the sample employs a flow cytometer, such as a Coulter counter. Another prior cell-counting procedure employs a photometric technique in which light is directed through a fluid-suspension of the cells. Photodetectors responsive to the resultant scattered light provide signals that are a measure of the quantity of cells in the suspension.

These known cytological procedures for quantizing cells have drawbacks, including requiring expensive equipment and having limited performance in terms of reliability, repeatability, accuracy and precision. They also present biohazard risks, including from the handling of biosamples.

It is accordingly an object of this invention to provide an improved method and apparatus for quantizing cells and other particles carried in a fluid medium. Specific objects are to provide such a method and apparatus for implementation at a relatively low cost, and for controllable automated operation with relatively high reliability, repeatability, accuracy and precision.

Other objects of the invention are to provide an improved method and apparatus for collecting a selected quantity of cells and other particles that are carried in a fluid medium, particularly in a liquid medium.

It is also an object of the invention to provide an improved method and apparatus for determining a quantitative measure of the flow condition of a screen-type filter device subject to obstruction by particles larger than a known threshold size.

Another object of the invention is to provide an improved method and apparatus for collecting a specified sample of cells for cytological examination.

Other objects of the invention will in part be obvious and will in part appear hereinafter.

GENERAL DESCRIPTION

In accordance with the invention, a quantitative measure responsive to the number of particles, e.g. cells, in a fluid medium is obtained by providing a screen-type filter device in a flow path for the particle-carrying fluid. A flow condition, e.g. a selected pressure or flow velocity as a function of time, is imposed on the fluid medium. A measurement is made of a parameter responsive to the resultant flow, including change in flow, through the filter device due to the applied flow condition. The invention further provides for determining a selected change in that measured parameter responsive to the obstruction of the filter device by particles larger than a threshold size.

As used herein, a screen-type filter device refers to a filter, such as a membrane filter, that blocks cells and other particles larger than a selected threshold size and that passes smaller particles essentially without obstruction. Such a filter device typically has a filtering surface that is progressively obstructed as it blocks an increasing number of particles above the threshold size.

The applied fluid condition can be a pressure signal that causes fluid to flow through the filter device. Examples include an applied pressure signal that remains essentially constant over a selected time interval. Another example is a succession of pressure pulses, typically of known magnitude, duration and time spacing. The applied flow condition can also be an applied fluid velocity through the filter device. Examples are to maintain a selected constant flow through the filter device, over a selected time interval, and to apply a succession of flow pulses.

The measurement of a parameter responsive to flow through the filter device due to the applied flow condition includes, in one practice of the invention, measuring the rate of flow in response to an applied uniform pressure signal. In another practice, it includes measuring the change in pressure across the filter device required to maintain a selected flow velocity. Another example is to measure the time required for the flow through the filter device to change by a selected amount, typically as measured by a change in flow rate for a given applied pressure or by a change in pressure to maintain a selected flow rate.

In accordance with a further practice of the invention, the applied condition, or applied flow signal, is a succession of pulses, and the measured parameter monitors the equilibration of the flow following each applied pulse. In one illustrative instance, the measured parameter is the time for the flow velocity to equilibrate to a selected relative level following application of a selected pressure pulse.

In one specific practice of the invention, a liquid suspension of cells flows under constant applied pressure through a membrane filter. The rate of fluid flow through the filter device is measured, typically either for a selected interval of time or until the flow rate decreases by a selected amount. The change in fluid flow through the filter device is directly responsive to the number or concentration of particles or cells in the liquid, because the filter blocks the cells of interest while passing smaller cells, and accordingly becomes increasingly blocked or clogged by the cells of interest.

In another specific practice of the invention, a succession of known pressure pulses, which can be of positive pressure or of negative pressure, is applied to drive the cell-carrying fluid through the filter device, and the time is measured after each pulse for the pressure across the filter device to return to a selected relative level, i.e. to equilibrate a selected amount.

When the measured equilibrate times have increased from the initial measure, i.e. for the initial pressure pulse, by a selected amount, a corresponding known quantity of cells has collected on the filter.

The practice of the invention thus, in one aspect, measures the flow condition of a screen type filter as it becomes increasingly obstructed, to determine a measure of particles in the fluid medium directed through the filter. The particles being measured in this indirect way have a size larger than a selected value determined by the pore size or other porosity measure of the filter screen.

The practice of the invention can thus provide a quantitative measure regarding particles in a fluid medium larger than a selected threshold value, and the measure is obtained indirectly, by applying the pressure and flow factors of Boyle's law with a screen-type filter. The quantitative measure can be of the number of particles, where the average size of the particles above the threshold value is known. Otherwise, the measure is of the relative area or portion of the filter surface that the particles cover.

The practice of invention further provides for collecting a selected quantity of cells or other particles carried in a liquid or other fluid medium. For this practice of the invention, continued flow of the fluid deposits progressively more particles above the threshold value on the filter surface. Thus an increasing area of the filter surface collects and is obstructed by additional particles. This obstruction of a known relative portion of the filter surface area corresponds directly with the collection of a known quantity of particles having a known average size larger than the threshold size. This quantitatively known collection of particles, which typically is obtained from an unknown quantity of particles in a sample liquid or other fluid, can be further processed, typically by removal of the collected particles from the filter device, or in response to a reverse pressure or reverse flow. One illustrative practice is to collect a selected quantity of cells in this manner and to subject the collected quantized cell sample to cytological examination, using known cytological testing techniques.

The invention further features a programmable control element that applies a selected flow signal for producing a flow of fluid that carries particles through the filter device, and for monitoring flow-responsive parameters, such as pressure across the filter or fluid flow through the filter. The programmable control element enables the practice of the invention to be automated, to have a controlled fluid flow or pressure change, and to stop or otherwise change the operation automatically, depending on the application.

A further feature of the invention provides an apparatus having a container for the fluid medium that carries the particles and having a vessel closed at one wall portion with a filter device that blocks passage of cells or other particles of interest. The vessel is disposed with the filter device immersed in the fluid in the container. In one specific cytological embodiment, the vessel disposes the filter device immersed below the level of a cell-carrying liquid in the container. A fluid source applies a selected flow condition to the filter device, causing the fluid medium to flow through the filter device from the container to the vessel. One or more sensors are provided for measuring one or more parameters responsive to the fluid flow through the filter device.

Another feature of the invention provides a chamber element in fluid communication with the vessel and container system for reducing the effect of changes in the height of the liquid therein.

The apparatus also has a source that applies a selected flow condition to the container-vessel system. The source can apply a selected pressure condition upon the filter device, or impose a selected fluid flow through it. In accord with a further feature of the invention, a further chamber element is provided to decrease the time for the pressure across the filter device to equilibrate after an applied pressure pulse, and thereby to speed up the overall time for measurement in accordance with the invention. This further chamber element has a volume closed to the atmosphere and greater than a volume associated with the filter vessel.

A further practice of the invention directs a flow of air carrying microscopic particles, for example, contaminants above a selected size, across a membrane filter that blocks particles of interest while passing smaller particles. When the average size of the particles above this threshold value is known, a measurement of the change of the fluid flow through the filter yields a precise and reliable measure of the quantity of the airborne particles. Further, this practice of the invention can collect a known quantity of the particles on the filter for further measurement or other processing.

The invention thus provides a method and apparatus for determining quantitative information regarding particles above threshold size, including airborne particles and biological cells, present in a fluid -- either gaseous or liquid -- indirectly, by a measurement of the fluid flow. The practice of the invention can employ relatively inexpensive measuring equipment that operates with dependability and accuracy and precision, and on a controllable automatic basis.

The invention accordingly comprises the several steps and the relation of one or more of such steps with respect to each of the others, and the apparatus embodying feature of construction, combinations of elements and arrangement of parts adapted to effect such steps, all as further exemplified in the following detailed disclosure, and the scope of the invention is indicated in the claims.

For a fuller understanding of the nature and objects of the invention, reference should be made to the following detailed description and the accompanying drawings, in which.

DESCRIPTION OF ILLUSTRATED EMBODIMENTS

Figure 1:
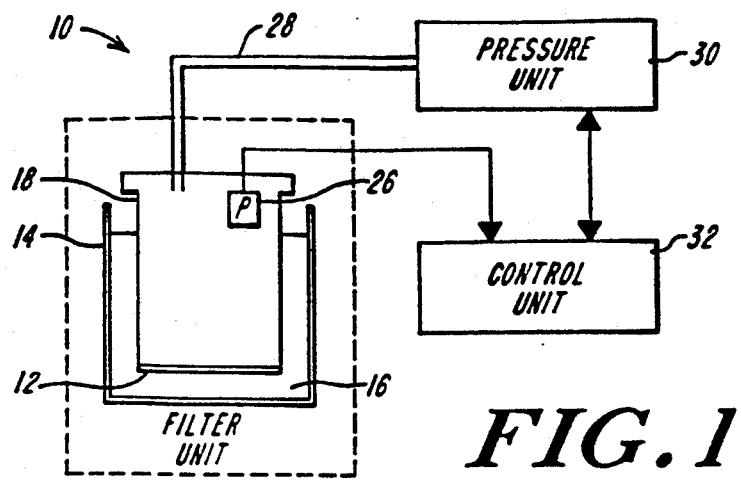
FIG. 1 is a schematic block diagram of particle quantizing apparatus according to one practice of the invention.

FIG. 1 shows a system 10 according to one practice of the invention for controlled instrumented processing of biological cells. The illustrated system collects a selected quantity of cells onto a screen-type filter 12. The system 10 has a specimen container 14 that contains a liquid 16 that carries the cells. The filter 12 is on the bottom wall of a collection vessel 18. The collection vessel is fitted within the specimen container 14 to immerse the filter 12 into the liquid 16 in the container 14.

Figure 2:
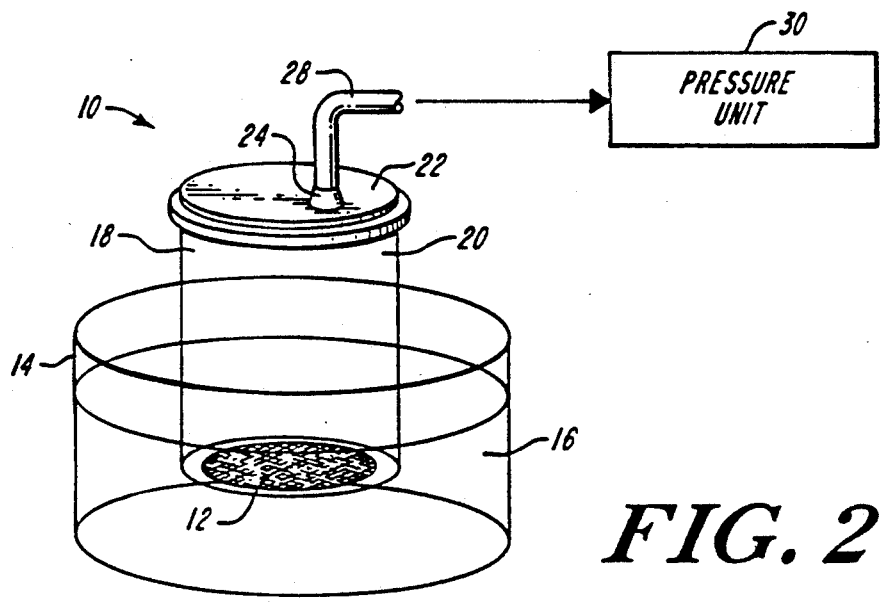
FIG. 2 shows a liquid container and filter vessel for use in the apparatus of FIG. 1.

The illustrated specimen container 14, as shown in FIG. 2, is open at the top to the atmosphere and can be an open vessel such as a cup, vial, or beaker. The illustrated collection vessel 18 has a cylindrical tubular body 20 with the filter 12 spanning and closing a normally lower axial end. The body 20 of the collection vessel 18 is fitted with a cap 22 at the other, normally upper end. The screen-type filter 12 is preferably a membrane filter and hence is apertured with a uniform distribution of pores of substantially uniform size to block cells and other particles above a threshold size determined by the size of the pores, and to freely pass smaller particles. The filter has a filtering surface, illustrated as an essentially flat disc that has a surface area of known or readily determined size.

The cap 22 that closes the top of the vessel 18, together with the body 20, renders the vessel pressure tight except at the filter 12 and at a port 24 in the cap. As shown in FIG. 1, the illustrated cap 22 also mounts a pressure transducer 26 arranged for sensing the pressure within the collection vessel 18, preferably at its normally upper end.

As further shown in FIG. 1, a pressure hose 28 connects the port 24 of the collection vessel 18 to a pressure unit 30, so that the pressure unit is in fluid communication with the interior of the collection vessel. An electronic control unit 32 connects with the pressure transducer 26 to receive a pressure-responsive electrical signal, and connects with the pressure unit 30.

The pressure unit 30, typically in response to electrical control signals from the control unit 32, which can be microprocessor controlled, applies selected fluid conditions to the interior of the collection vessel 18. More particularly, the control unit 32 and pressure unit 30 operate the illustrated system 10 to collect a selected quantity of cells onto the underside of the filter 12, from a sample carried in the liquid 16 and wherein the cells have a known average size above the filter pore size, i.e. above a selected threshold size, and otherwise are of unknown quantity.

For this operation, the pressure unit 30, typically in response to signals from the control unit 32, applies a flow condition to the interior of the collection vessel 18 to create a selected flow of liquid from the specimen container to the collection vessel, by way of the filter 12. This flow of liquid carries cells to the filter, which accordingly becomes progressively covered and hence blocked by the cells. The pressure unit 30 applies the selected flow condition to the collection vessel until the filter becomes clogged by a selected amount, as determined at least in part by the pressure sensed within the vessel 18 by means of the transducer 26.

Figure 3:
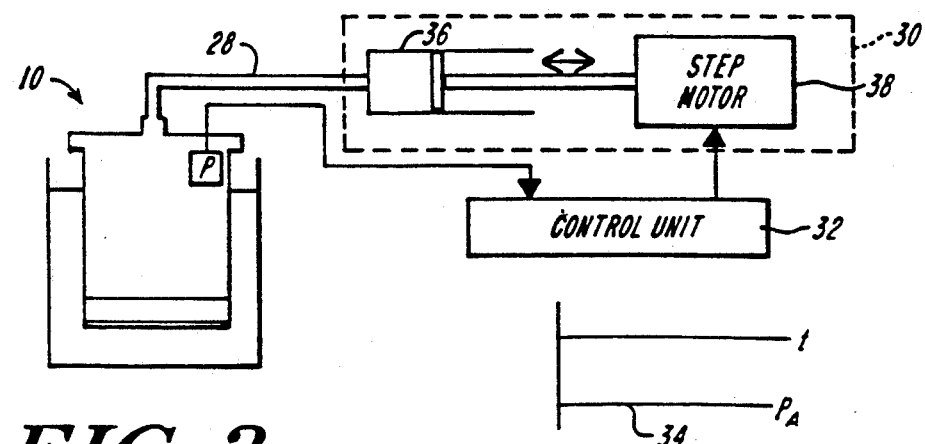
FIG. 3 is a schematic representation of the FIG. 1 system illustrating operation with a constant applied pressure signal.

FIG. 3 illustrates one such operating sequence in which the applied pulse signal from the pressure unit 30 is a constant selected negative pressure within the collection vessel 18. The constant applied pressure across the filter 12 produces a flow of liquid 16 from the container 14 into the vessel 18, through the filter 12. The flow decreases with time, due to progressive obstruction of the filter by cells in the liquid. A measure of a parameter responsive to the change in flow rate accordingly provides a quantitative measure of the surface of the filter clogged by cells in the liquid, i.e. of the increase in filter clogging by the cells, and of the number of cells above the filter threshold size, assuming the average size of such cells is known.

For this illustrated embodiment, the pressure unit 30 can employ a displacement pump, such as a piston pump 36 driven by a stepping motor 38. The control unit 32 monitors the pressure in the collection vessel, by way of the transducer 26, and controls the stepping motor pulses required to maintain the constant applied pressure. When the timing of the stepping motor pulses slows by, for example, ten percent from the initial rate to maintain the selected applied pressure, the system 10 has collected a quantity of cells that covers ten percent of the filter surface. When the control unit terminates operation at this juncture, with a sample of cells having known average size above the filter threshold size, a correspondingly known quantity of cells is collected on the surface of the filter 12 and can if desired, be transferred from the filter to, for example, a microscope slide for image analysis either visually or by machine vision or both. The transfer of the collected cells from the filter 12 to a microscope slide can be carried out by applying a slight mechanical pressure within the vessel 18 against the filter 12, e.g. by pressing an alcohol-bearing sponge against the filter, after microscope slide is brought into contact with the filter 12, to essentially lift the cells off the filter 12 to adhere to the microscope slide. U.S. Pat. No. 4,395,493 discloses one practice of this type of transfer of cells from a filter type object to a microscope slide.

The embodiment of FIG. 3 thus operates with an applied pressure signal and measures a time parameter, i.e. the rate of stepping motor pulses, responsive to the resultant flow rate through the filter device, thereby to provide an indirect quantitative measure.

Figure 4:
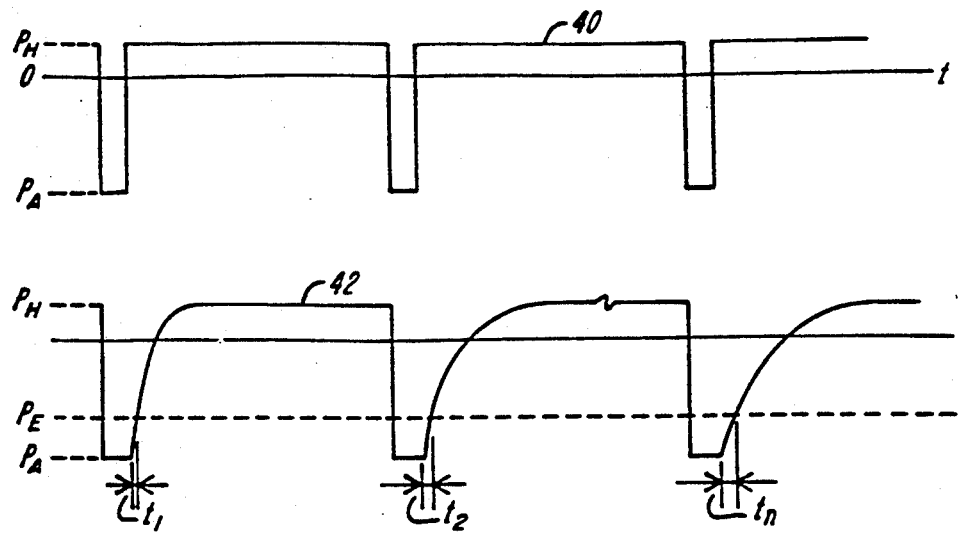
FIG. 4 shows graphs illustrating operation of the FIG. 1 system with a pulsed pressure signal.

FIG. 4 illustrates operation of the FIG. 1 system 10 with a pressure source 30 and a control unit 32 arranged to apply a sequentially pulsed flow signal, illustrated by waveform 40, and to measure the time for the pressure within the vessel 18, i.e. across the filter 12, to equilibrate after each applied pulse to a selected level $P_E$. The FIG. 4 waveform 42 illustrates the pressure within the vessel 18 and hence across the filter 12 which the pressure sensor 26 senses.

The signal waveforms in FIG. 4 do not reveal the changes in the pressure head $P_H$, during this operation. The pressure head decreases during operation by a relatively small and significant amount, depending on the densities of the fluids in container 14 and in vessel 18. Accordingly, in the illustrated embodiment, the pressure head decreases as the levels of liquid 16 in the container and in the vessel change in response to each applied pressure pulse.

The FIG. 4 waveform 40 of pressure pulses which the pressure unit 30 applies to the collection vessel 18, and hence across the filter 12 since the collection container 14 is open to the atmosphere, shows that each pulse reduces the pressure within the vessel 18 from a positive pressure head value designated $P_H$ to a selected small negative value designated $P_A$. Each illustrated applied pressure pulse has a negative $P_A$ value of 0.050 psi. This specific value, and others stated herein, are by way of example only and the invention can be practiced with other values as those skilled in the art will determine in accord with this description. The pulses repeat at a rate such that the pressure within the vessel 18, i.e. the vessel pressure, returns before each new pulse is applied to a value slightly below the value of the pressure head prior to the last applied pressure pulse.

The waveform 42 of the vessel pressure that results from the applied flow condition is normally at the $P_H$ value, and drops to the $P_A$ value in response to each applied pulse. After each applied pulse terminates, the vessel pressure gradually returns to the $P_H$ value, as liquid flows from the sample container 14 through the filter 12 into the collection vessel 18. The pressure returns at an exponential rate.

The control unit 32 monitors the time, after application of an applied pressure pulse, for the vessel pressure of waveform 42 to equilibrate from the $P_A$ value toward the $P_H$ value to a selected equilibrate level $P_E$. The rate of pressure return is responsive to the degree of clogging of the filter, and accordingly gradually slows as an increasing portion of the filter surface becomes covered by and hence clogged by cells larger than the filter threshold size. The monitored equilibrate time $t_1, t_2, \ldots t_n$ therefore increases in direct proportion to the rate at which the filter clogs with cells.

The control unit 32 stops the pressure unit 30 from applying further pressure pulses when the equilibrate time has increased by a selected amount from the initial time $t_1$. The increase in equilibrate time is selected to correspond to a selected increase in filter obstruction, which in turn corresponds to the collection of a selected quantity of cells from the sample liquid 16 onto the filter 12. By way of example, a system as shown in FIG. 1 and operating as described with reference to FIG. 4 with pressure pulses each having a value of 0.050 pound per square inch and with a filter 12 having surface area of approximately three square centimeters, transfers in the order of fifty microliters of liquid from the sample container 14 into the filter vessel 18 with each applied pressure pulse. The system accordingly measures the cells within the liquid at essentially a liquid drop at a time, for each applied pressure pulse.

Figure 5:
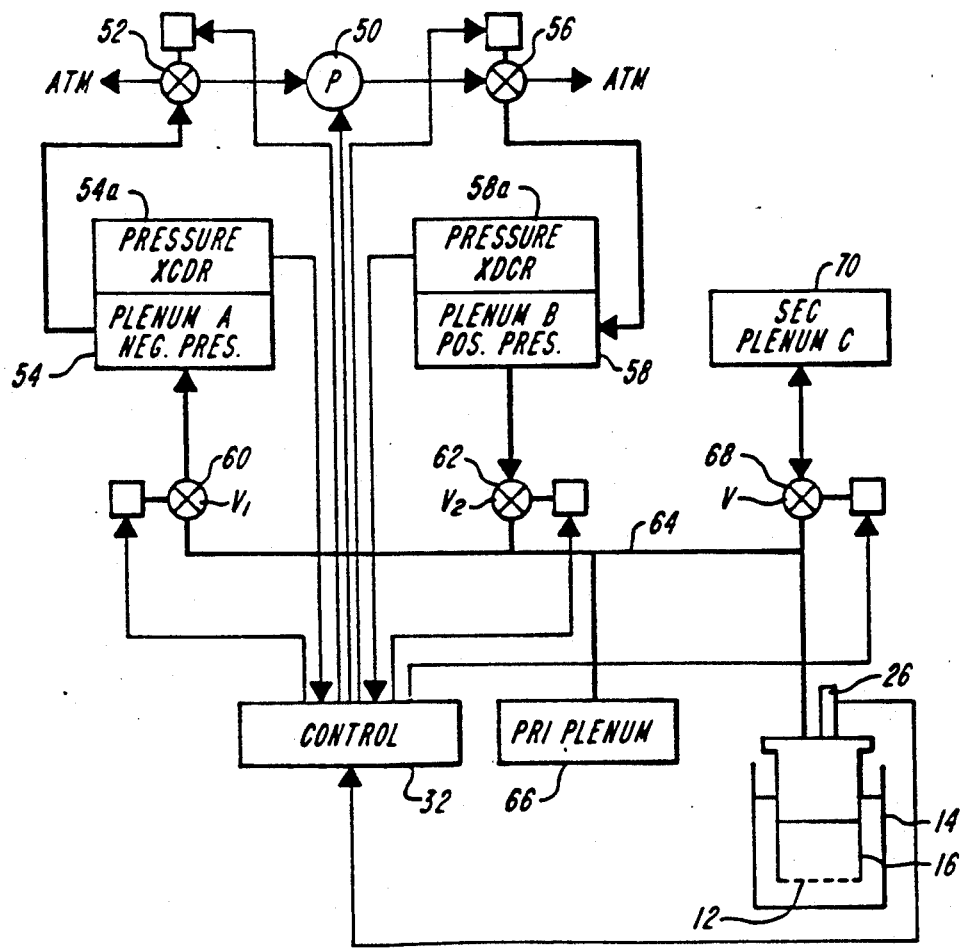
FIG. 5 is a block schematic representation of a pressure unit according to the invention.

FIG. 5 shows a construction for the pressure unit 30 preferred for the foregoing pulsed operation of the system of FIG. 1 as illustrated in FIG. 4. The illustrated pressure unit construction embodies two further features, one of which diminishes measuring errors due to a change in the pressure head, i.e. a decrease in the pressure head as liquid is drawn from the sample container 14 into the filter collection vessel 18. A second feature speeds the equilibration of the vessel pressure to the $P_H$ value, and thereby reduces the time required to attain a given collection of cells on the filter 12.

In the illustrated pressure unit, a pump 50 is connected by way of a valve 52 to maintain a selected negative pressure in a plenum 54, and is connected by way of a valve 56 to maintain a selected positive pressure in a plenum 58. A valve 60 connects the pressure in plenum 54 with the collection vessel 18, by way of a pressure line 64. A further valve 62 applies the positive pressure in plenum 58 to the pressure line 64 leading to the collection vessel 18. Each plenum 54 and 58 preferably is fitted with a pressure transducer 54a and 58a, respectively, and electrical leads connect the pump 50, each valve 52, 56, 60 and 62 and each plenum pressure transducer to control circuits within the control unit 32.

A primary auxiliary plenum 66 is coupled in communication with the pressure line 64, and a valve 68 selectively couples a secondary auxiliary plenum 70 in communication with the pressure line 64, the valve 68 is operated by the control unit.

The control unit 32 operates the pump and the valves 52 and 56 to maintain a selected negative pressure, e.g. $-0.25$ psi, in the plenum 54 and to maintain a selected positive pressure, e.g. $+0.50$ psi, in the plenum 58. The auxiliary plenum 66 is in direct communication by way of the pressure line 64 with the pressure vessel and accordingly is at the same pressure. The secondary auxiliary plenum 70 is coupled to be at the pressure of the collection vessel 18 when the valve 68 is open.

In the illustrated embodiment, the combined fluid volume of collection vessel 18, when empty of liquid, and of the pressure line 64 between the vessel 18 and the valves 60, 62 and 68 is in the order of ten cubic centimeters. The volume of each plenum 54 and 58 is typically two orders of magnitude or more larger. The volumes of the primary plenum 66 and of the secondary plenum 70 are selected to balance one another and the combined volumes of the vessel 18 and pressure lines 64, for the pulsed and equilibrate operation described further below. In the illustrated embodiment, the primary plenum 66 has a volume of approximately twenty cubic centimeters and the secondary plenum 70 has a volume of approximately 250 cubic centimeters.

One sequence for operating the system 10 of FIG. 1 as shown in FIG. 4 with the pressure unit 30 of FIG. 5 commences with opening the valve 60 to wet the filter 12 with a small volume of fluid from the sample container 14. (Unless stated otherwise, this and other operations described herein proceed with the valves 60, 62 and 68 in normally closed condition.) The valve 60 is then closed, and the valve 62 is opened to apply positive pressure to the collection vessel for driving liquid therein outward through the filter 12, to empty the collection vessel 18 and to remove any cells and other particles from the filter 12.

With the filter 12 thus wet with the liquid in the container 14 and the collection vessel and the filter cleared of fluid and of cells, the operation illustrated in FIG. 4 commences with valve 60 open for brief intervals to apply the pressure pulses $P_A$ as shown in waveform 40. The control unit 32 continues this operation with the pressure unit and with monitoring the pressure in the collection vessel 18 to determine the equilibrate times, until the equilibrate time has increased by the selected margin relative to the initial value $T_1$. The control unit 32 then stops the operation, with a selected quantitative measure of cells collected on the filter 12.

More particularly, prior to applying each pressure pulse and with the filter vessel 18 at the head pressure corresponding to the difference in liquid level between the vessel 18 and the container 16, the control unit 32 opens valve 68 to allow the pressure in the secondary plenum 70 to equilibrate to that pressure head. The control unit 32 then closes the secondary plenum valve 68 and applies a pressure pulse to the filter chamber 18 by opening valve 60 and monitoring vessel pressure with the transducer 26. When the pressure transducer signal indicates that the vessel pressure has dropped from the head value, $P_H$, to the desired applied pressure, $P_A$, the control unit 32 closes valve 60.

The resultant pressure differential across the filter 18 causes liquid to flow from the container 16 into the vessel 18 and hence across the filter 12. The rate of flow, and correspondingly the pressure difference, diminish at an exponential rate. During this time, all three valves 60, 62, and 68 are closed.

When the control unit 32 senses that the vessel pressure has dropped to the selected equilibrate level and has measured the corresponding time interval $T_n$, the control unit 32 opens the secondary plenum valve 68, to speed the return of the pressure vessel to the $P_H$ value immediately prior to the last applied pressure pulse.

The volumes of the plenums 66 and 70 and of the collection vessel 18 and pressure line 64 are selected so that, when the valve 68 is opened after the filter vessel pressure has equilibrated to the $P_E$ value, the head-pressure value stored in the secondary plenum 70—corresponding to head pressure prior to the last applied pressure pulse—brings the vessel pressure to a level close to, yet less than the head pressure. A relatively small further liquid flow across the filter 12 accordingly fully equilibrates the vessel pressure to a new, slightly lesser, head pressure.

Thus the secondary plenum 70, in essence, stores a pressure corresponding in value to the head pressure prior to the application of a pressure pulse, and speeds up return of the vessel pressure to a new, lesser head pressure corresponding to conditions after application of that pressure pulse. The illustrated system preferably avoids the condition where the stored pressure in a secondary plenum 70, upon opening a valve 68 after the vessel pressure is at the equilibrate value causes a reverse flow of liquid from the vessel 18 into the container 16. Such a reverse flow condition is considered disadvantageous for the illustrated operation and accordingly is avoided.

The primary plenum 66 is in parallel with and augments the collection vessel pressure, to minimize the effect of changes in pressure head. This plenum also is sized to match, or balance, the desired dynamic range of volume of the filter vessel 18, between conditions of being empty and conversely filled with liquid from the container 16, for the foregoing speed-up operation with the selected volume of the secondary plenum 70. Thus, the primary plenum 66 preferably has the smallest volume that, relative to the volume of the collection vessel 18 and pressure line 64, accommodates the dynamic range of filter vessel capacity change, without back flow of liquid outward from the vessel 18 through the filter 12. The ratio of volume in the secondary plenum 70 to the combined volumes of the primary plenum 66 and the collection vessel 18 and pressure line 64 is preferably in the order of approximately ten to one.

The foregoing arrangement of the pressure unit 30, as illustrated in FIG. 5, thus enables the illustrated system to have a small collection vessel 18 and to operate with relatively low sensitivity to changes in the height of liquid therein relative to the liquid height in the sample container 14. This reduction in sensitivity to changes in the pressure head enhances measuring accuracy and precision. The arrangement also allows the system to employ a compact and relatively inexpensive collection vessel 18 that may be discarded after each measurement for precluding intersample contamination.

It will thus be seen that the invention efficiently attains the objects set forth above, among those made apparent from the preceding description. It will also be understood that changes may be made in the above construction and in the foregoing sequences and operation without departing from the scope of the invention. It accordingly is intended that all matter shown in the accompanying drawings be interpreted as illustrative rather than in any limiting sense.

It is also to be understood that the following claims are intended to cover all of the generic and specific features of the invention as described herein, and all statements of the scope of the invention which, as a matter of language, might be said to fall therebetween.

Having described the invention, what is claimed as new and secured by Letters Patent is:

1. Apparatus for supplying a selected sequence of pressure conditions to a filter device for controlling the flow of particle-containing fluid through the filter device, said apparatus comprising
   A. means forming a filter chamber having pressure port means and having a filter device forming a chamber wall thereof and having a porosity for blocking particles of selected size, said filter chamber being arranged for fluid to flow into the interior thereof through said filter device,
   B. pressure source means arranged with valve means for selectively applying a source pressure to said chamber interior by way of said pressure port means, said source pressure being different from a first pressure in said filter chamber and producing a flow of fluid greater than any flow occurring during presence of said first pressure, and
   C. control means arranged for sensing the chamber interior pressure and connected with said valve means, said control means being arranged for executing a cycle of successive operations including
      (i) a first step of opening said valve means for applying said source pressure to said chamber interior for producing a selected fluid flow through said filter device,
      (ii) a second step of closing said valve means for allowing a flow of fluid through said filter device for equilibrating the chamber pressure in a direction from said source pressure toward said first interior pressure,
      (iii) a third step of measuring an equilibration time in which said chamber pressure equilibrates from said source pressure to a second chamber pressure intermediate said first pressure and said source pressure, said equilibration time corresponding to a degree of blockage of said filter device by the particles, and
      (iv) repeating said first and second and third steps only in response to an equilibration time, as measured in said third step, less than a predetermined time value.

2. Apparatus according to claim 1 further comprising
   A. means forming plenum means arranged with plenum valve means for selectively coupling said plenum means with said filter chamber, and
   B. means for establishing in said plenum means, at least prior to the initial occurrence of said first step, a pressure for producing said first pressure in said filter chamber,
   C. said control means being further arranged for executing said cycle of operations including
      (i) closing said plenum valve means during said first step, said second step and said third step, and
      (ii) opening said plenum valve means for coupling said plenum means with said filter chamber after said measured chamber interior pressure has reached said second chamber pressure.

3. Apparatus according to claim 2 in which said filter chamber has a first volume and in which said plenum means has a volume at least one order of magnitude greater than said first volume.

4. Apparatus according to claim 1 further comprising plenum means coupled in parallel with said filter chamber.

5. Apparatus according to claim 1 further comprising
A. first plenum means coupled in parallel with said filter chamber,
B. second plenum means arranged with plenum valve means for selectively coupling said second plenum means with said filter chamber, said filter chamber and said first plenum means together having a first combined volume, and said second plenum means having a volume at least one order of magnitude greater than said first combined volume, and
C. means for establishing in said second plenum means, at least prior to the initial occurrence of said first step, a pressure for producing said first pressure in said filter chamber,
D. said control means being further arranged for executing said cycle of operations including
  (i) closing said plenum valve means during said first step, said second step and said third step, and
  (ii) opening said plenum valve means for coupling said second plenum means with said filter chamber after said measured chamber interior pressure has reached said second chamber pressure.

6. Apparatus for measuring the occlusion of a filter device by particles contained in a fluid flowing through the filter device, said apparatus comprising
A. means forming a filter chamber having a filter device forming a chamber wall thereof and having a porosity for blocking particles of selected size, said filter chamber being arranged for fluid to flow into the interior thereof through said filter device,
B. pressure source means arranged with valve means for selectively applying a flow-producing pressure differential across said filter device, said flow-producing pressure differential being different from a first pressure differential across said filter device and producing a flow of fluid greater than any flow occurring during presence of said first pressure differential, and
C. control means arranged for sensing a pressure differential across said filter device and connected with said valve means, said control means being arranged for executing a cycle of successive operations including
  (i) a first step of opening said valve means for applying said flow-producing pressure differential across said filter device for producing a selective fluid flow through said filter device,
  (ii) a second step of closing said valve means for allowing a flow of fluid through said filter device for equilibrating the pressure differential in a direction from said flow-producing pressure differential toward said first pressure differential,
  (iii) a third step of measuring an equilibration time in which said pressure differential equilibrates from said flow-producing pressure differential to an equilibration pressure differential intermediate said first pressure differential and said equilibration pressure differential, and
  (iv) repeating said first and second and third steps only in response to an equilibration time, as measured in said third step, less than a predetermined time value.

7. A method for supplying a selected sequence of pressure conditions to a filter device for controlling the flow of particle-containing fluid through the filter device, said method comprising
A. providing a filter chamber having pressure port means and having a filter device forming a chamber wall thereof and having a porosity for blocking particles of selected size, said filter chamber being arranged for fluid to flow into the interior thereof through said filter device,
B. providing a pressure source arranged with valve means for selectively applying a source pressure to said chamber interior by way of said pressure port means, said source pressure being different from a first pressure in said filter chamber and producing a flow of fluid greater than any flow occurring during presence of said first pressure,
C. providing control means arranged for sensing the chamber interior pressure and connected with said valve means,
D. operating said control means through a cycle of successive operations including
  (i) a first step of opening said valve means for applying said source pressure to said chamber interior for producing a selected fluid flows through said filter device,
  (ii) a second step of closing said valve means for allowing a flow of fluid through said filter device for equilibrating the chamber pressure in a direction from said source pressure toward said first interior pressure,
  (iii) a third step of measuring an equilibration time in which said chamber pressure equilibrates from said source pressure to a second chamber pressure intermediate said first pressure and said source pressure, and
  (iv) repeating said first and second and third steps only in response to an equilibration time, as measured in said third step, less than a predetermined time value.

* * * * *